United States Patent [19]

Larsson et al.

[11] Patent Number: 5,533,804
[45] Date of Patent: Jul. 9, 1996

[54] PROCESS FOR PREPARING A STOCK SOLUTION COMPOSITION FOR A MEDICAL TREATMENT, AND A SOFT BAG HAVING A MAGNETIC STIRRER TO BE USED IN THE PREPARATION OF SAID STOCK SOLUTION COMPOSITION

[75] Inventors: Ake Larsson, Tokyo; Kiyoshi Uno, Shiga, both of Japan

[73] Assignee: Gambro KK, Japan

[21] Appl. No.: 307,653

[22] PCT Filed: Mar. 5, 1993

[86] PCT No.: PCT/SE93/00191

§ 371 Date: Sep. 19, 1994

§ 102(e) Date: Sep. 19, 1994

[87] PCT Pub. No.: WO93/18805

PCT Pub. Date: Sep. 30, 1993

[30] Foreign Application Priority Data

Mar. 19, 1992 [JP] Japan ................... 3-063695

[51] Int. Cl.⁶ .................. B01F 13/08; A61J 1/10; A61J 1/14
[52] U.S. Cl. .................. 366/274; 604/416; 604/903
[58] Field of Search ................... 366/273, 274, 366/348; 416/3; 383/127; 206/219, 220, 221, 818; 604/56, 82, 92, 403, 416, 903; 215/DIG. 3, DIG. 8

[56] References Cited

U.S. PATENT DOCUMENTS

| | | |
|---|---|---|
| 3,306,829 | 2/1967 | Patterson et al. . |
| 3,328,255 | 6/1967 | Ilg ................... 604/903 X |
| 3,399,040 | 8/1968 | Ilg ................... 604/903 X |
| 3,647,397 | 3/1972 | Coleman ................ 366/273 X |
| 4,008,717 | 2/1977 | Kowarski . |
| 4,784,495 | 11/1988 | Jonsson et al. . |
| 5,226,878 | 7/1993 | Young ................... 604/416 X |
| 5,344,231 | 9/1994 | Jonsson et al. . |
| 5,348,389 | 9/1994 | Jonsson et al. . |
| 5,385,564 | 1/1995 | Slater et al. . |

FOREIGN PATENT DOCUMENTS

| | | | |
|---|---|---|---|
| 33292 | 8/1981 | European Pat. Off. ........ 604/903 |
| 034916 | 9/1981 | European Pat. Off. . |
| 49553 | 4/1982 | European Pat. Off. ........ 206/220 |
| 278100 | 8/1988 | European Pat. Off. ........ 604/56 |
| 402611 | 12/1990 | European Pat. Off. . |
| 3520361 | 12/1986 | Germany ................ 366/273 |
| 4017868 | 10/1990 | Germany . |

*Primary Examiner*—Charles E. Cooley
*Attorney, Agent, or Firm*—Lerner, David, Littenberg, Krumholz & Mentlik

[57] ABSTRACT

Processes for the preparation of stock solutions for use in medical treatments such as dialysis including the steps of providing a flexible bag containing powder components of the stock solution, supplying water to the flexible bag to provide the stock solution, and dissolving the powder in the water within the flexible bag by stirring the powder by application of a magnetic field to a magnetic stirrer disposed within the bag.

11 Claims, 1 Drawing Sheet

PROCESS FOR PREPARING A STOCK SOLUTION COMPOSITION FOR A MEDICAL TREATMENT, AND A SOFT BAG HAVING A MAGNETIC STIRRER TO BE USED IN THE PREPARATION OF SAID STOCK SOLUTION COMPOSITION

FIELD OF THE INVENTION

The present invention relates to processes for preparing stock solution compositions for medical treatments. More particularly, the present invention relates to such processes for use in medical treatments such as dialysis, hemodialysis, hemofiltration or hemodiafiltration. Still more particularly, the present invention relates to a soft and/or flexible bag intended to be used for such stock solution preparations. Still more particularly, the present invention relates to processes for preparing stock solution compositions for medical treatments for use in blood dialysis, and particularly in the dialysis by means of artificial kidneys. Still more particularly, the present invention relates to soft or flexible bags to be used for preparing such stock solution compositions.

BACKGROUND OF THE INVENTION

Solutions of specified compositions for medical use in connection with blood dialysis have been commercially prepared by drug manufacturers in the form of stock solution compositions having a predetermined concentration. Such stock compositions can then be supplied to hospitals and other facilities having therapeutic dialysis facilities. For example, such stock solution compositions, comprising the necessary components at a predetermined concentration, are filled in 10 liter containers comprising materials such as polyethylene, and commercially supplied through commission agents to hospitals or the like having dialysis facilities. In the case of so-called "bicarbo solution compositions for dialysis," which have been widely used in recent years, it is necessary to prepare not only a conventional stock solution composition for the dialysis procedures, but also a concentrated bicarbo solution composition. Therefore, as far as bicarbo solution compositions are concerned, the above-mentioned two kinds of stock solution compositions are separately filled in two separate containers, and supplied to therapeutic dialysis facilities.

At present, conventional stock solutions for dialysis procedures are transported and supplied in the form of a liquid, therefore creating many problems, as discussed below. For example, such conventional compositions in the form of a liquid are therefore of undesirably large weight and volume, so that they are very inconvenient to transport, as well as to store and handle. Furthermore, after use of these solutions, a large number of emptied polyester containers or the like remain in these dialysis facilities, and it may therefore be rather difficult for these facilities to discard the emptied containers in an appropriate manner.

SUMMARY OF THE INVENTION

The present inventors have thus carried out various studies for the purpose of providing improved stock solution compositions for dialysis procedures, which can be conveniently transported and stored, and which can be easily formulated into preparations ready for use in such dialysis. As a result of these studies, the inventors have now discovered that an improved stock solution composition for the dialysis procedure can be prepared quite easily according to a method in which soft or flexible bags are produced, each of which contains powder components of a stock solution composition for the dialysis, in addition to a stirrer. These soft bags are transported and supplied to dialysis facilities, and when using the powder components for the dialysis, a predetermined amount of water is supplied to the soft bag to dissolve the powder components in the water with the aid of the stirrer, whereby the aimed stock solution composition can be easily prepared. On the basis of this finding, the present invention has been completed.

According to this invention, a process for the preparation of a stock solution has now been provided for use in a medical treatment comprising providing a flexible bag containing components of the stock solution in the form of a powder, supplying a predetermined amount of water to the powder in order to provide the stock solution at a predetermined concentration within the flexible bag, and dissolving the powder in the water within the flexible bag by stirring the powder by application of a magnetic field thereto.

In accordance with a preferred embodiment of the process of the present invention, the medical treatment can be dialysis, hemodialysis, hemofiltration and/or hemodiafiltration. Preferably, the predetermined amount of water comprises a predetermined amount of a water solution. In a preferred embodiment, providing the flexible bag includes providing a stirrer in the flexible bag which is actuatable by means of application of the magnetic field.

In accordance with another embodiment of the process of the present invention, the flexible bag has a volume which is sufficiently large to contain the powder and the predetermined amount of water. Preferably, providing the flexible bag includes providing a stirrer in the flexible bag which is actuatable by means of application of the magnetic field. In a preferred embodiment, the stirrer has a weight and a size which are preselected to minimize the time required to completely dissolve the powder.

In accordance with another embodiment of the process of the present invention, stirring of the powder is carried out at a stirring rate of from about 500 to 1000 RPM. In another embodiment, dissolving of the powder is carried out at a temperature of about 37° C.

According to the present invention, a process for preparing a stock solution composition for the blood dialysis is provided which is characterized by the fact that a predetermined amount of water is supplied to a soft bag containing powder components of the stock solution composition and having a stirrer, and in which the powder components are dissolved in the water with stirring by means of the stirrer.

The present invention also preferably relates to a soft bag to be used in preparing a stock solution composition for the blood dialysis, and in which the soft bag contains powder components of the stock solution composition for the blood dialysis, and also contains a stirrer.

BRIEF DESCRIPTION OF THE DRAWING

The following detailed description can be more readily understood with reference to the drawing, in which.

DETAILED DESCRIPTION

Figure 1:
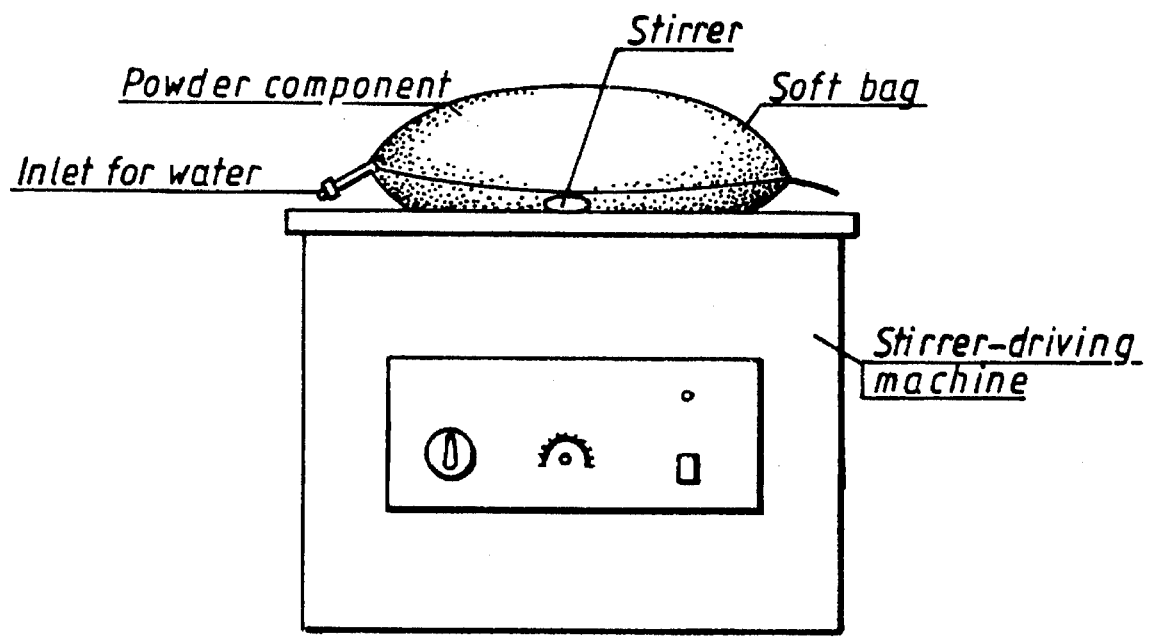
FIG. 1 is a partially schematic representation of an embodiment of the process of the present invention.

The soft or flexible bags to be employed in the present invention can be any soft bags made for conventional medical uses. Preferred examples of such soft bags include soft bags made from soft polyvinyl chlorides.

Powder components of stock solution compositions which are to be put in such soft bags may be those which are conventionally used in the art. For instance, when stock solution compositions for acetate dialysis are to be prepared, the soft bags are previously charged with predetermined amounts of sodium chloride, potassium chloride, calcium chloride, magnesium chloride, sodium acetate and glucose. For preparing stock bicarbo solution compositions for dialysis, a soft bag for solution (A) is previously charged with the same powder components as those used for acetate dialysis, and another soft bag for solution (B) is previously charged with a predetermined amount of sodium hydrogen carbonate (sodium bicarbonate).

There are no specific limitations on stirrers to be placed within these soft bags. Preferably, however, use is made of stirrers coated with Teflon. It is satisfactory to put one stirrer in one soft bag. The size and weight of a stirrer can be readily selected by considering the amount of stock solution composition which is to be prepared. For instance, if two liters of water are to be supplied to prepare a stock solution composition, it is preferred to use a stirrer having a weight of from about 10 to 15 g, and a length of from about 40 to 60 mm.

A soft bag according to the present invention can be prepared in a manner in which the soft bag is charged with the above-mentioned powder components and provided with a stirrer, and the soft bag is then subjected to a conventional sterilization operation, and thereafter to a conventional packing operation.

When a stock solution composition is to be prepared by employing a soft or flexible bag according to the present invention, the bag is charged with a predetermined amount of distilled water or RO-water (i.e., water produced by means of reverse osmosis), and thereafter the soft bag is placed on a stirrer-rotating machine, which is then rotated to effect stirring, and therefore to dissolve the powder components in the water so as to form the desired stock solution composition. The dissolving operation may usually be performed at room temperature, although it is also possible to effect a stirring operation at a higher temperature, for instance, of about 37° C., in order to prepare the desired stock solution composition in a short period of time. There is no specific limitation on the rotation speed of stirrer, although it is preferred to rotate the stirrer at a speed of about 1,000 RPM in the case of preparing two liters of stock solution composition.

An embodiment of the present invention is illustrated in FIG. 1. Referring to FIG. 1, a schematic view, is shown which illustrates an embodiment in which about six liters of water are supplied to a soft bag having a size of about 30×20 cm, and which is provided with a stirrer having a weight of 12 g and a length of 50 mm. The stirrer is rotated on a stirrer-rotating machine to prepare a stock solution composition for dialysis.

According to the present invention, soft bags are charged with powder components to be used for preparing stock solution compositions for the dialysis, and the soft bags are further provided with stirrers. Thus, the soft bags are intended to be used to prepare stock solution compositions for the dialysis. The soft bags according to this invention are very light and have a small volume, and therefore the soft bags are convenient to transport and to store. In addition, when using the soft bags, it is very easy to prepare stock solution compositions in a short period of time.

The present invention can be further illustrated by the Example set forth below.

EXAMPLE

Soft bags according to the present invention were prepared by using either the following stock solution composition for acetate dialysis, or the below-mentioned stock solution composition for bicarbo dialysis. Various tests were then carried out on these bags.

| Stock solution composition for acetate dialysis | |
|---|---|
| | (in 100 ml) |
| Sodium chloride (NaCl) | 20.25 g |
| Potassium chloride (KCl) | 0.52 g |
| Calcium chloride ($CaCl_2.2H_2O$) | 0.65 g |
| Magnesium chloride ($MgCl_2.6H_2O$) | 0.53 g |
| Sodium acetate ($CH_3COONa.3H_2O$) | 15.78 g |
| Glucose ($C_6H_{12}O_6$) | 7.00 g |

| Stock solution composition for bicarbo dialysis | |
|---|---|
| | (in 100 ml) |
| Solution A | |
| Sodium chloride (NaCl) | 21.270 g |
| Potassium chloride (KCl) | 0.522 g |
| Calcium chloride ($CaCl_2.2H_2O$) | 0.772 g |
| Magnesium chloride ($MgCl_2.6H_2O$) | 0.356 g |
| Sodium acetate ($CH_3COONa.3H_2O$) | 1.720 g |
| Glucose ($C_6H_{12}O_6$) | 3.500 g |
| Solution B | 7.00 g |
| Sodium Hydrogen carbonate ($NaHCO_3$) | |

Soft bags (30×15 cm), made from soft polyvinyl chloride, were individually charged with the above-mentioned powder components. Thereafter, 2000 ml of distilled water were supplied to each soft bag, and dissolution tests were made under the conditions shown below.

(I) Test on stirrers

Procedures:

Measurements were made to determine the time required to completely dissolve all of the components in water, when various stirrers were used. In this test, use was made of three types of stirrers, having the weights and lengths shown below.

(1) Weight—12.6 g; Length—50 mm (2) Weight—6.6 g; Length—51 mm (3) Weight—4.0 g; Length—30 mm The temperature was 20° C., and the rotation speed of the stirrers was 500 RPM.

Results:

In the case of the stock solution composition for acetate dialysis:

(1) 12'30"

(2) 14'00"

(3) Not complete dissolved even after 30'.

In the case of the stock solution composition for bicarbo dialysis:

| | Solution A | Solution B |
|---|---|---|
| (1) | 6'30" | 8'30" |
| (2) | 7'00" | 9'00" |
| (3) | Not completely dissolved even after 30'. | Not completely dissolved even after 30'. |

Therefore, it can be seen that, when using the above-mentioned soft bags, the stirrers of type (1) or (2) may preferably be employed.

(II) Test concerning the rotation speed
Procedures
Measurements were made to determine the time required to completely dissolve all of the components in the case where the dissolving operations were effected under stirring by means of a stirrer operated at various rotational speeds. The following three rotational speeds were employed:

(1) 100 RPM
(2) 500 RPM
(3) 1000 RPM

The temperature was 20° C., and use was made of the stirrer of type (1) mentioned in Test (1).
Results:
In the case of the stock solution composition for acetate dialysis:

(1) Not completely dissolved even after 30'.
(2) 12'30"
(3) 10'30"

In the case of the stock solution composition for bicarbo dialysis:

|  | Solution A | Solution B |
| --- | --- | --- |
| (1) | Not completely dissolved even after 30'. | Not completely dissolved even after 30'. |
| (2) | 6'30" | 8'30" |
| (3) | 6'0" | 8'00" |

From the above, it can be seen that the stirrer should preferably be operated at a rotation speed of from about 500 to 1000 RPM.

(III) Test on temperature of Solvent
Procedures:
Measurements were made to determine the time required to completely dissolve all of the components, when the solvent, namely distilled water, is supplied at various temperatures. The following two temperatures were employed in this test.

(1) 20° C.
(2) 37° C.

Use was made of the stirrer of type (1) mentioned in Test (I). The rotational speed of the stirrer was 500 RPM.
Results:
In the case of the stock solution composition for acetate dialysis:

(1) 12'30"
(2) 9'00"

In the case of the stock solution composition for bicarbo dialysis:

|  | Solution A | Solution B |
| --- | --- | --- |
| (1) | 6'30" | 8'30" |
| (2) | 5'00" | 2'30" |

From the above, it can be seen that the dissolving operation should preferably be carried out at a temperature of about 37° C.

The invention has above been described in connection with dialysis and with a soft bag containing a stirrer. It can, however, also be used for the preparation of other medical liquids, such as liquids intended for hemofiltration or hemodiafiltration. Furthermore, it is to be noted that the powder components may also be dissolved without the use of a stirrer, if a magnetic field is provided which directly influences an electrolytic solution of the type used, for instance, for dialysis.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A process for the preparation of a stock solution for use in dialysis, hemodialysis, hemofiltration, or hemodiafiltration comprising: providing a container which is a soft flexible bag, said bag containing components of said stock solution useful in dialysis, hemodialysis, hemofiltration or hemodiafiltration, said components being in the form of a powder, providing a magnetic stirrer within said bag, supplying a predetermined amount of water into said bag, placing said bag in direct contact with a source of a magnetic field, and dissolving said powder in said water within said flexible bag at a temperature of about room temperature or above, to provide a stock solution at a predetermined concentration by stirring said powder and said water together by the application of said magnetic field to said magnetic stirrer, said powder being dissolved and stirred without said bag being placed in any other container.

2. The process of claim 1 wherein said predetermined amount of water comprises a predetermined amount of a water solution.

3. The process of claim 1 wherein said flexible bag has a volume sufficiently large to contain said powder and said predetermined amount of water.

4. The process of claim 1 wherein said stirrer has a weight and size preselected to minimize the time required to completely dissolve said powder.

5. The process of claim 4 wherein said stirring of said powder is carried out at a stirring rate of from about 500 to 1000 rpm.

6. The process of claim 4 wherein said dissolving of said powder is carried out at a temperature of about 37° C.

7. A process for the preparation of a stock solution for use in dialysis, hemodialysis, hemofiltration, or hemodiafiltration comprising: providing a container which is a soft flexible bag, said bag containing components of said stock solution including a bicarbonate in the form of a powder, providing a magnetic stirrer within said bag, supplying a predetermined amount of water into said bag, placing said bag in direct contact with a source of a magnetic field, and dissolving said powder in said water within said flexible bag at a temperature of about room temperature or above, to provide a stock solution at a predetermined concentration by stirring said powder and said water together said powder being dissolved and stirred without said bag being placed in any other container.

8. The method of claim 7 wherein said stock solution is dissolved at a temperature of about 37° C.

9. The method of claim 8 wherein said magnetic stirrer is operated at a speed of approximately 500 rpm or greater.

10. The method of claim 7 wherein said magnetic stirrer is operated at a speed of approximately 500 rpm or greater.

11. The method of claim 7 wherein said stock solution is heated to a temperature of about 37° C.

* * * * *

UNITED STATES PATENT AND TRADEMARK OFFICE
CERTIFICATE OF CORRECTION

PATENT NO.   : 5,533,804
DATED        : July 9, 1996
INVENTOR(S)  : Larsson et al.

It is certified that error appears in the above-indentified patent and that said Letters Patent is hereby corrected as shown below:

Column 6, line 54, in claim 7, after "together" insert --by the application of said magnetic field to said magnetic stirrer such that said stirrer rotates at greater than 100 RPM,--.

Signed and Sealed this

Twelfth Day of November, 1996

Attest:

BRUCE LEHMAN

*Attesting Officer*     *Commissioner of Patents and Trademarks*